(12) United States Patent
Bae et al.

(10) Patent No.: US 7,993,375 B2
(45) Date of Patent: Aug. 9, 2011

(54) DYNAMIC STABILIZATION DEVICES AND METHODS

(75) Inventors: Hyun Bae, Santa Monica, CA (US); John Pafford, Eads, TN (US)

(73) Assignee: Spine Wave, Inc., Shelton, CT (US)

( * ) Notice: Subject to any disclaimer, the term of this patent is extended or adjusted under 35 U.S.C. 154(b) by 819 days.

(21) Appl. No.: 11/950,754

(22) Filed: Dec. 5, 2007

(65) Prior Publication Data
US 2008/0161854 A1 Jul. 3, 2008

Related U.S. Application Data

(60) Provisional application No. 60/868,646, filed on Dec. 5, 2006.

(51) Int. Cl.
*A61B 17/70* (2006.01)
(52) U.S. Cl. ........ 606/257; 606/246; 606/261; 606/263; 623/17.11
(58) Field of Classification Search .......... 606/246–279, 606/300–321; 623/17.11
See application file for complete search history.

(56) References Cited

U.S. PATENT DOCUMENTS

| | | | |
|---|---|---|---|
| 3,997,138 | A | 12/1976 | Crock et al. |
| 4,697,582 | A | 10/1987 | William |
| 4,743,260 | A | 5/1988 | Burton |
| 5,562,660 | A | 10/1996 | Grob |
| 5,672,175 | A | 9/1997 | Martin |
| 6,290,700 | B1 | 9/2001 | Schmotzer |
| 6,530,929 | B1 | 3/2003 | Justis et al. |
| 6,616,667 | B1 | 9/2003 | Steiger et al. |
| 6,802,844 | B2 * | 10/2004 | Ferree .................. 606/258 |
| 6,986,771 | B2 | 1/2006 | Paul et al. |
| 6,989,011 | B2 | 1/2006 | Paul et al. |
| 7,008,422 | B2 | 3/2006 | Foley et al. |
| 7,011,660 | B2 | 3/2006 | Sherman et al. |
| 7,188,626 | B2 | 3/2007 | Fokley et al. |
| 7,250,052 | B2 | 7/2007 | Landry et al. |

(Continued)

FOREIGN PATENT DOCUMENTS
EP    0 140 790 B1    3/1989
(Continued)

OTHER PUBLICATIONS

PCT Search Report, PCT Patent Application, PCT/US07/86495, 9 pages.

(Continued)

*Primary Examiner* — Eduardo C Robert
*Assistant Examiner* — Christina Negrelli
(74) *Attorney, Agent, or Firm* — Hoffmann & Baron, LLP

(57) ABSTRACT

A dynamic stabilization device includes end caps that define a bore for receiving a corresponding bone screw therethrough. A spacer is engaged between each end cap and a cable passes through each of the components and is placed in tension to couple the spacer between the two end caps. The spacer is formed of a material that allows some flexible movement after implantation. An alternative stabilization device includes a spacer over-molded about two bushings defining the bores. According to a method of use, a stabilization device is passed along guide wires through a small incision. Once the device is in contact with the vertebrae, the bone screws are advanced along the guide wires and driven into the bone. One fastener bore may include a camming surface that causes distraction of the vertebrae as the bone screw is threaded into the vertebral bone.

21 Claims, 7 Drawing Sheets

U.S. PATENT DOCUMENTS

| | | |
|---|---|---|
| 7,833,251 B1 | 11/2010 | Ahlgren et al. |
| 2001/0037111 A1 | 11/2001 | Dixon et al. |
| 2003/0040746 A1 | 2/2003 | Mitchell et al. |
| 2004/0236328 A1* | 11/2004 | Paul et al. ............ 606/61 |
| 2004/0267279 A1 | 12/2004 | Casutt et al. |
| 2005/0010220 A1 | 1/2005 | Casutt et al. |
| 2005/0065515 A1 | 3/2005 | Jahng |
| 2005/0177157 A1 | 8/2005 | Jahng |
| 2005/0203517 A1 | 9/2005 | Jahng et al. |
| 2005/0288672 A1 | 12/2005 | Ferree |
| 2006/0052783 A1* | 3/2006 | Dant et al. ............ 606/61 |
| 2006/0084987 A1* | 4/2006 | Kim ............ 606/61 |
| 2006/0106381 A1 | 5/2006 | Ferree et al. |
| 2006/0122620 A1 | 6/2006 | Kim |
| 2006/0129149 A1 | 6/2006 | Iott et al. |
| 2006/0142761 A1 | 6/2006 | Landry et al. |
| 2006/0241597 A1 | 10/2006 | Mitchell et al. |
| 2006/0264940 A1 | 11/2006 | Hartmann |

FOREIGN PATENT DOCUMENTS

| | | |
|---|---|---|
| EP | 0669109 B1 | 8/1995 |
| FR | 2777449 | 10/1999 |

OTHER PUBLICATIONS

1988 Orthopaedics: Richards Annual Product Catalog, 1988, Richards Medical Company, 1450 Brooks Road, Memphis, TN 38116, 6 pages.

Swanson, Todd V., "THA Using Minimally Invasive Posterior Approach vs. Standard Posterior Approach", Las Vegas, Mevada, www.minitotalhip.com, 2 pages.

Keggi, John; Emerson, Roger; Fisher, David and Keggi, Kristaps Roundtable, "Beyond Definitions to Approaches and Insights", Nov./Dec. 2004, www.orthopedictechreview.com/issues/novdec04/pg29.htm, downloaded Nov. 12, 2007, 8 pages.

Stulberg, David S., "Minimally Invasive Navigated Knee Surgery: An American Perspective", Orthopedics, Oct. 2005; 28:1241, www.orthosupersite.com, 7 pages.

\* cited by examiner

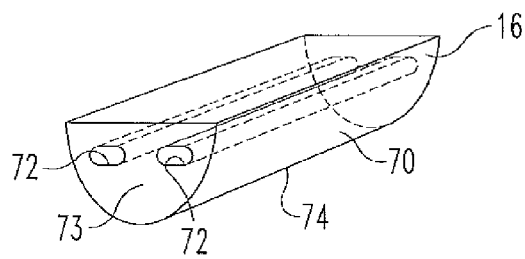
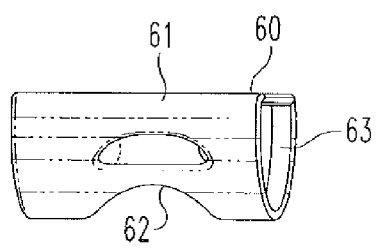
Fig. 12        Fig. 13
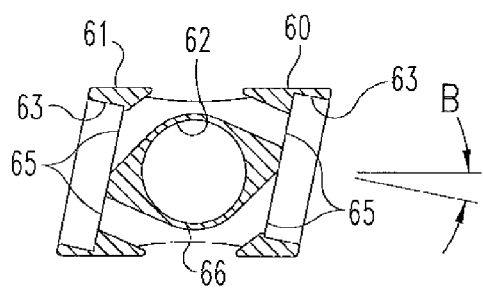
Fig. 14
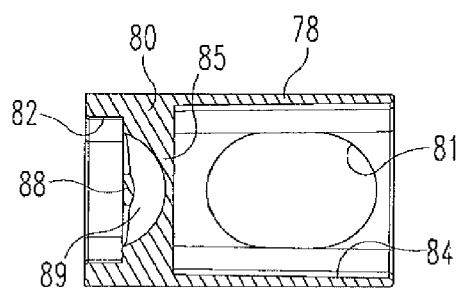
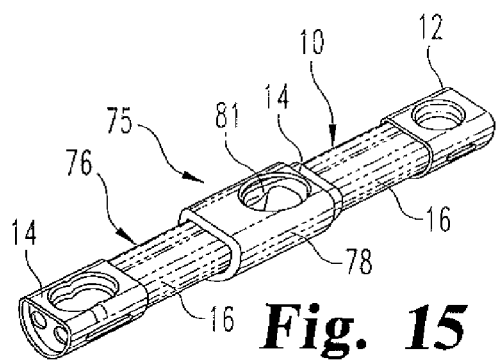
Fig. 16        Fig. 15
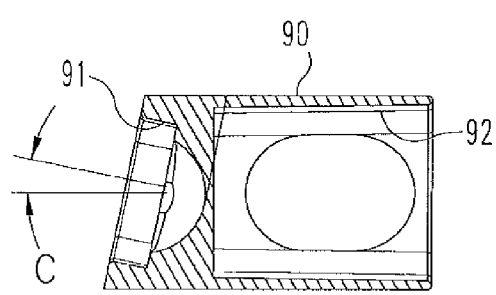
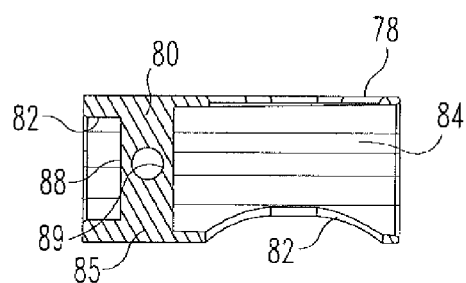
Fig. 18        Fig. 17

DYNAMIC STABILIZATION DEVICES AND METHODS

BACKGROUND

The present invention relates to spinal stabilization systems and particularly to semi-rigid devices for fixation to the vertebrae.

Degenerative spinal column diseases, such as disc degenerative diseases (DDD), spinal stenosis, spondylolisthesis, and so on, often need surgical operation if conservative pain management approaches prove inadequate. Typically, spinal decompression is the first surgical procedure that is performed. The primary purpose of decompression is to reduce pressure in the spinal canal and on nerve roots located therein by removing certain tissue of the spinal column to reduce or eliminate the pressure and pain caused by the pressure. If the tissue of the spinal column is removed the pain is reduced but the spinal column is weakened. Therefore, fusion surgery (e.g., ALIF, PLIF or posterolateral fusion) is often necessary for spinal stability following the decompression procedure. However, following the surgical procedure, fusion takes additional time to achieve maximum stability and a spinal fixation device is typically used to support the spinal column until a desired level of fusion is achieved. Depending on a patient's particular circumstances and condition, a spinal fixation surgery can sometimes be performed immediately following decompression, without performing the fusion procedure. The stabilization surgery is performed in most cases because it provides immediate postoperative stability and, if fusion surgery has also been performed, it provides support of the spine until sufficient fusion and stability has been achieved.

Conventional methods of spinal fixation utilize a rigid spinal fixation device to support an injured spinal segment and prevent movement of the injured part. These conventional spinal fixation devices include: fixing screws configured to be inserted into the pedicle or sacrum of the spinal vertebrae to a predetermined depth and angle, rods or plates configured to be positioned adjacent to the injured spinal segment, and coupling elements for connecting and coupling the rods or plates to the fixing screws such that the injured spinal part is supported and held in a relatively fixed position by the rods or plates.

U.S. Pat. No. 6,193,720 discloses a conventional spinal fixation device, in which connection members of a rod or plate type are mounted on the upper ends of at least one or more screws inserted into the spinal pedicle or sacrum of the backbone. The connection units, such as the rods and plates, are used to stabilize the injured part of the spinal column which has been weakened by decompression. The connection units also prevent further pain and injury to the patient by substantially restraining the movement of the spinal column. However, because the connection units prevent normal movement of the spinal column, after prolonged use the spinal fixation device itself can cause ill effects, such as "junctional syndrome" (transitional syndrome) or "fusion disease" resulting in further complications and abnormalities of the spinal column. In particular, due to the high rigidity of the rods or plates used in conventional fixation devices, the patient's treated segments are not allowed to move after the surgical operation, and the movement of the spinal motion segments located superior or inferior to the instrumented vertebral level is increased. Consequently, such spinal fixation devices may eventually lead to decreased mobility of the patient and increased stress and instability to the spinal motion segments adjacent to the instrumented level.

It has been reported that excessive rigid spinal fixation is not helpful to the fusion process due to decreased or abnormal load sharing caused by rigid fixation. Thus, load sharing semi-rigid spinal fixation devices have been developed to eliminate this problem and assist the bone fusion process. For example, U.S. Pat. No. 5,672,175, U.S. Pat. No. 5,540,688 and U.S. Pub No 2001/0037111 disclose dynamic spine stabilization devices having flexible designs that permit axial load translation (i.e., along the vertical axis of the spine) for bone fusion promotion. However, because these devices are intended for use following a bone fusion procedure, they are not well-suited for spinal fixation without fusion. Thus, in the end result, the problems resulting from fusion still persist with these devices.

To solve the above-described problems associated with rigid fixation, non-fusion technologies have been developed. The Graf band is one example of a non-fusion fixation device that is applied after decompression without bone fusion. The Graf band is composed of a polyethylene band and pedicle screws to couple the polyethylene band to the spinal vertebrae requiring stabilization. The primary purpose of the Graf band is to prevent sagittal rotation (flexion instability) of the injured spinal motion segments. Another non-fusion fixation device called "Dynesys" is similar to the Graf band except it uses a polycarbonate urethane (PCU) spacer between the screws to maintain the distance between the heads of two corresponding pedicle screws and, hence, adjacent vertebrae in which the screws are fixed. Early reports by the inventors of the Dynesys device indicate it has been successful in many cases. However, due to the mechanical configuration of the device, the surgical technique required to attach the device to the spinal column is complex and complicated.

U.S. Pat. Nos. 5,282,863 and 4,748,260 disclose a flexible spinal stabilization system and method using a plastic, non-metallic rod. U.S. patent publication No. 2003/0083657 discloses another example of a flexible spinal stabilization device that uses a flexible elongate member. These devices are flexible but they are not well-suited for enduring long-term axial loading and stress. Additionally, the degree of desired flexibility versus rigidity may vary from patient to patient. The design of existing flexible fixation devices are not well suited to provide varying levels of flexibility to provide optimum results for each individual candidate. For example, U.S. Pat. No. 5,672,175 discloses a flexible spinal fixation device which utilizes a flexible rod made of metal alloy and/or a composite material. Additionally, compression or extension springs are coiled around the rod for the purpose of providing de-rotation forces on the vertebrae in a desired direction. Prior flexible rods such as that mentioned in U.S. Pat. No. 5,672,175 typically have solid construction with a relatively small diameter in order to provide a desired level of flexibility. Because they are typically very thin in an effort to provide suitable flexibility, such prior art rods may be prone to mechanical failure.

Additionally, in a conventional surgical method for fixing the spinal fixation device to the spinal column, a doctor incises the midline of the back to about 10-15 centimeters, and then, dissects and retracts the soft tissue to both sides. In this way, the doctor performs muscular dissection to expose the outer part of the facet joint. Next, after the dissection, the doctor finds an entrance point to the spinal pedicle using radiographic devices (e.g., C-arm fluoroscopy), and inserts securing members of the spinal fixation device (referred to as "spinal pedicle screws") into the spinal pedicle. Thereafter, the connection units (e.g., rods or plates) are attached to the upper portions of the pedicle screws in order to provide support and stability to the injured portion of the spinal column.

Thus, in conventional spinal fixation procedures, the patient's back is incised substantially and as a result the back muscles important for maintaining spinal column stability are incised or injured, leading to significant post-operative pain to the patient and a slow recovery period.

To reduce patient trauma, minimally invasive surgical procedures have been recently developed which are capable of conducting spinal fixation surgery through a relatively small hole or "window" that is created in the patient's back at the location of the surgical procedure. Through this smaller incision or window, two or more securing members (e.g., pedicle screws) of the spinal fixation device are screwed into respective spinal pedicle areas using a navigation system. Thereafter, special tools are used to connect the stabilizing members (e.g., rods or plates) of the fixation device to the securing members. Alternatively, or additionally, the surgical procedure may include inserting a step dilator into the incision and then gradually increasing the diameter of the dilator. Thereafter, a tubular retractor is inserted into the dilated area to retract the patient's muscle and provide a visual field for surgery. After establishing this visual field, decompression and, if desired fusion procedures, may be performed, followed by a fixation procedure, which includes the steps of finding the position of the spinal pedicle, inserting pedicle screws into the spinal pedicle, using an endoscope or a microscope, and securing the stabilization members (e.g., rods or plates) to the pedicle screws in order to stabilize and support the weakened spinal column.

While these minimally invasive surgical procedures have done much to reduce the trauma and ill effects associated with spinal surgery, the nature of the implant itself can aggravate even a minimally invasive procedure. The nature of these fixation devices often requires significant manipulation at the surgical site, thereby complicating the procedure.

Therefore, conventional spinal fixation devices have not provided a comprehensive and balanced solution to the problems associated with addressing the effects of spinal diseases. Many of the prior devices are characterized by excessive rigidity, which leads to the problems discussed above, while others, though providing some flexibility, are not well-adapted to provide long-term stability and/or varying degrees of flexibility. The need exists for an improved dynamic spinal fixation device that provides a desired level of flexibility to the injured parts of the spinal column, while also providing long-term durability and consistent stabilization of the spinal column.

SUMMARY

In order to address these needs, a stabilization device is provided for implantation in the spine of a patient that comprises a pair of rigid end pieces, each defining a bore for receiving a bone engaging fastener therethrough, and an elongated spacer engaging each of the end pieces to maintain the end pieces at a predetermined spacing relative to each other. This spacing is adapted to orient the bore of each of the end pieces with respect to a corresponding vertebra of the patient, and more particularly to a point of fixation on each vertebra, such as the pedicle. The spacer is substantially rigid in compression along an axis parallel to the length of the spacer between the end pieces. In order to provide the necessary flexibility in the fixation, the spacer is relatively more flexible in degrees of freedom other than in compression. Thus, in one embodiment, the spacer is formed of a material such as PEEK (polyetheretherketone), polyurethane, polyphenolsulfone, polysulfone, acetal (including Delrin), polyethylene, or composites thereof.

In another aspect, the bore of at least one of the pair of end pieces is elongated parallel to the axis. This elongated bore defines a slot configured to receive the head of a bone engaging fastener extending through the elongated bore, in which the slot is contoured to move the head of the fastener away from the spacer as the fastener extends farther into the bore. Thus, when the stabilization device is positioned against the vertebrae to be instrumented, tightening a bone screw into this elongated bore will generate a distraction force to move the adjacent vertebrae apart.

In one embodiment, each of the pair of end pieces is a bushing and the elongated spacer is an elastomeric body over-molded about the end pieces. In another embodiment the end pieces include end caps with inboard projections, and the elongated spacer is an elastomeric body over-molded onto the projections. In yet another embodiment, the elongated spacer is an elastomeric body and each of the pair of end pieces is an elongated end cap having an end recess configured to receive an end of the elastomeric body therein. In this latter embodiment, the overall length of the stabilization device can be adjusted by selecting among several spacers having different lengths. With this feature, in one method of implanting the stabilization device a first step is to determine the distance between the bone anchoring locations for construct. In a specific approach, the distance between pedicles of adjacent vertebrae is measured. A spacer is then selected in accordance with that measured length, which will vary according to the patient and the anatomy of instrumented spinal level. When no distraction is necessary, the length of the spacer is selected so that the distance between screw bores is equal to the inter-pedicle distance. When distraction is desired, the spacer is selected so that the distance between the inboard end of the elongated bore and the non-elongated bore is equal to the inter-pedicle distance. In this case, as the bone screw is tightened into the bone through the elongated bore, the head of the bone screw will slide outboard until it reaches the outboard end of the elongated bore. This feature will thus distract the space between the instrumented vertebrae by essentially the length of the elongated bore.

In some cases, the stabilization device must adopt different angular orientation sin order to accommodate the anatomy of the "gutter". Thus, in some embodiments, the end recess of at least one of the pair of end caps is oriented at an angle relative to a longitudinal axis of the end cap. With this embodiment, when the spacer is engaged within the end recesses of the two end caps, one end cap will assume an angle relative to the longitudinal axis of the spacer.

In the embodiment of the stabilization device that includes separate end caps and spacer, the components are held together by a tensioning element coupling the spacer to the pair of end caps. In one embodiment, the tensioning element includes a cable and the spacer and pair of end caps define a passageway for receiving the cable in a loop therearound. The ends of the cable include an element for anchoring the cable to at least one of the end caps. In a specific embodiment, the anchoring element includes a crimp formed at each end of the cable, each crimp engaging one of the pair of end caps to maintain the cable in tension within the passageway.

The dynamic stabilization device may be adapted to create multi-level constructs—i.e., spanning more than two vertebrae. In this embodiment, one of the pair of end caps includes an end cap recess defined at a face of the end cap facing away from the spacer. This end cap recess is sized to receive an end cap of another stabilization device therein to form the multi-level construct. To accommodate variable spinal anatomies, the end recess of the one end cap may be oriented at an angle relative to the end cap recess.

In accordance with one preferred embodiment, the stabilization device is configured to rest snugly within the "gutter" formed by a transverse process and a facet of a corresponding vertebra of the patient. Thus, the lower portion of the end caps and spacer may assume a rounded trapezoidal configuration that corresponds to the shape of this "gutter" and that allows the device to bear directly against the pedicle of the vertebrae.

The dynamic stabilization device is preferably anchored to the vertebrae by bone screws each having a threaded shank configured for threaded engagement in vertebral bone and a head sized to prevent passage through a corresponding bore in the end pieces. The bores include a fastener engagement surface and the head of each bone screw and the corresponding engagement surface may be mutually configured to permit orientation of the bone screw at a range of angles relative to the end piece. In alternative embodiments, one or more of the interfaces between the bone screw and the engagement surface may be mutually configured to permit fixation of the head of the bone screw relative to the end piece.

A method for stabilizing a motion segment of the spine of a patient, comprises the steps of making an incision at the location of the motion segment, introducing a K-wire into at least two vertebrae to be stabilized and then placing a stabilization device onto each K-wire. The stabilization device includes rigid end pieces defining a bore corresponding to each K-wire and a spacer engaging the end pieces. In one aspect of the method, the length of the incision is less than the length of the stabilization device being implanted. Thus, the device is introduced through the incision at an angle.

Once within the subcutaneous space, the stabilization device is advanced along each K-wire until the device contacts the vertebrae. With the K-wires still in place, a bone screw is advanced onto each K-wire and through the corresponding fastener bore in the stabilization device. The bone screws are then threaded into a corresponding vertebra to anchor the stabilization device to the vertebrae. As discussed above, if the stabilization device is configured with an elongated fastener bore, threading the bone screw into that bore will distract the instrumented vertebrae.

A further method for stabilizing a motion segment of the spine of a patient, comprises the steps of determining the distance between two vertebrae of the motion segment to be stabilized, making an incision adjacent the location of the motion segment, in which the length of the incision is less than this distance, placing a guide member onto each of the vertebrae, guiding a stabilization device along each of the guide members through the incision until the stabilization device contacts the vertebrae, and then securing the stabilization device to the vertebrae.

DESCRIPTION OF THE FIGURES

FIG. 12 is a side perspective view of a spacer component of the dynamic stabilization device shown in FIG. 3.

FIG. 13 is a side elevational view of an angled end cap component according to an alternative embodiment of the invention.

FIG. 14 is a top cross-sectional view of the angled end cap shown in FIG. 13.

FIG. 15 is a top perspective view of a dynamic stabilization device according to a further embodiment of the present invention.

FIG. 16 is a top cross-sectional view of a boot component of the dynamic stabilization device depicted in FIG. 15.

FIG. 17 is a side cross-sectional view of the boot component shown in FIG. 16.

FIG. 18 is a top cross-sectional view of an angled boot component according to an alternative embodiment of the invention.

DESCRIPTION OF THE ILLUSTRATED EMBODIMENTS

Figure 1:
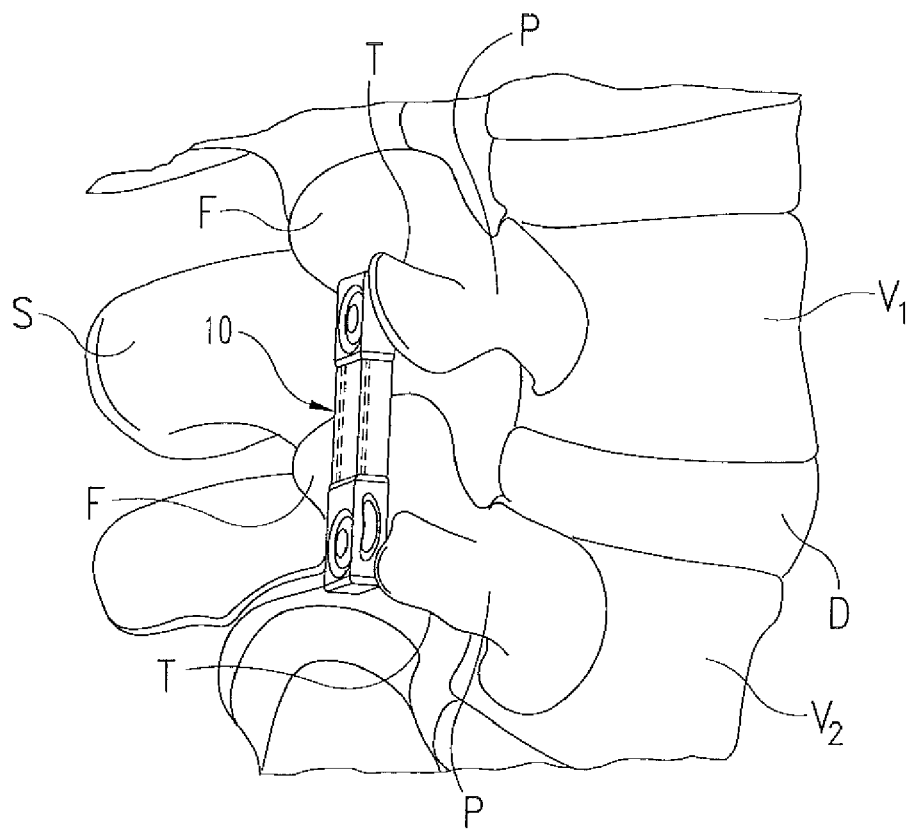
FIG. 1 is a lateral perspective view of a spinal motion segment instrumented with a dynamic stabilization device according to one embodiment of the present invention.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

A dynamic stabilization device 10 according to one embodiment is shown in FIG. 1 spanning the intervertebral disc D between adjacent vertebrae V1 and V2. As shown, the device 10 is seated within the "gutter" formed by the transverse processes T and the facet F. Not only is the device 10 situated anterior to the spinous processes S, it is also recessed or seated snugly the "gutter" for a low profile or prominence within the spine. This aspect of the device 10 allows it to be positioned closer to the center of rotation of the vertebra to provide more natural kinematics for the motion segment. In the arrangement shown in FIG. 1, the stabilization device may be anchored to the vertebrae V1, V2 by bone fasteners engaged to the pedicles P of the vertebrae, as will be described herein.

Figure 2:
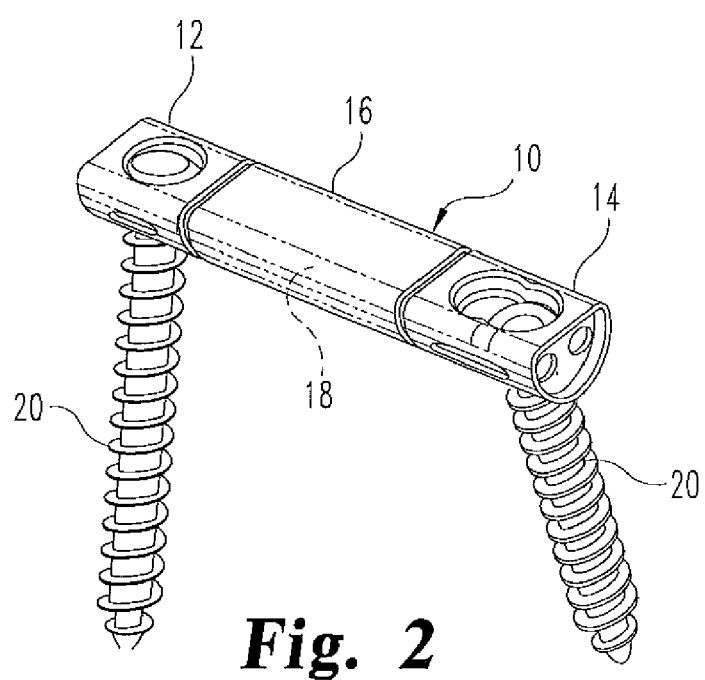
FIG. 2 is a top perspective view of the dynamic stabilization device shown in FIG. 1.
Figure 3:
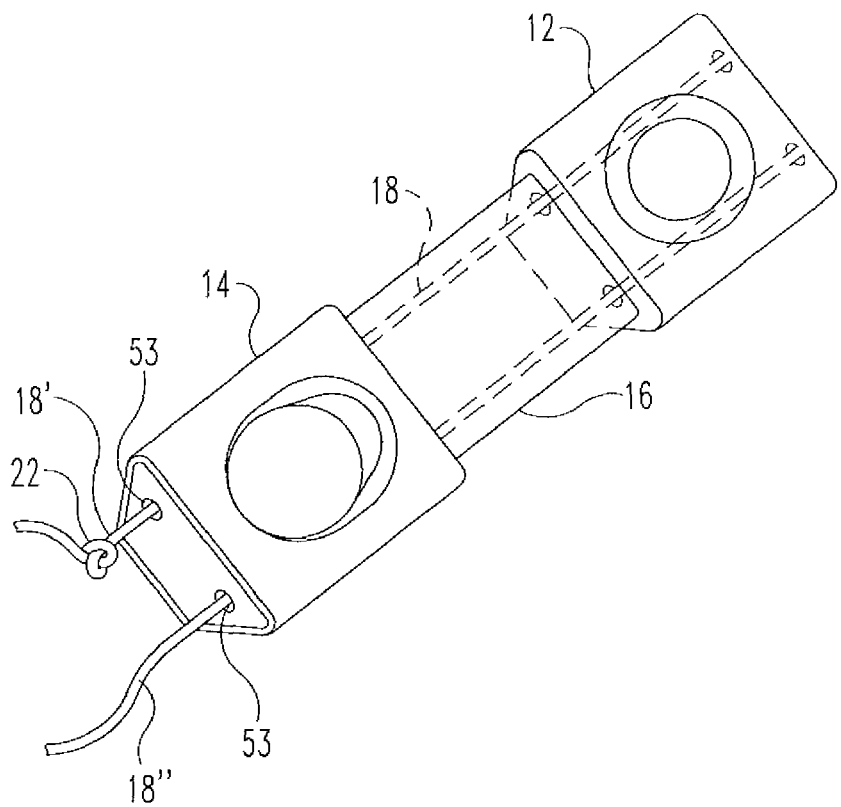
FIG. 3 is a top perspective view of the dynamic stabilization device shown in FIG. 2 without the bone engaging fasteners.
Figure 4:
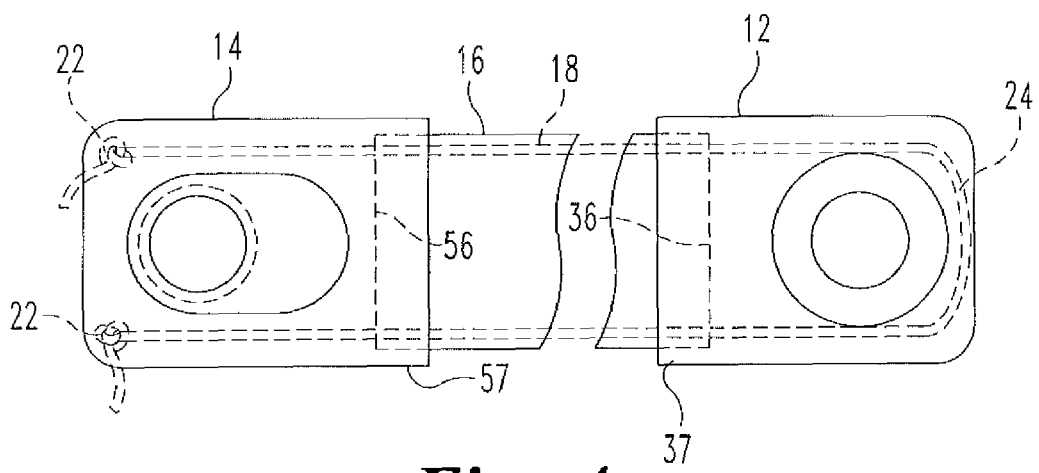
FIG. 4 is a top elevational view of the dynamic stabilization device depicted in FIG. 3.

The components of the dynamic stabilization device 10 are shown in FIGS. 2-4. In particular, the device includes a pair of end pieces at the opposite ends of the device that are configured to support bone engaging fasteners to engage corresponding vertebrae to be instrumented with the device. Thus, in one embodiment, the pair of end pieces includes a fixed position end cap 12 and a slotted end cap 14 that are configured to produce vertebral segment distraction in use, as explained in more detail below. The end caps are separated by a spacer 16. A tension element or cable 18 is used to fasten the end caps and spacer together. Bone engaging fasteners, such as bone screws 20, extend through each end cap for engagement with the associated vertebra, and more particularly the associated pedicle P.

In one embodiment, the ends of the cable 18 are anchored to one of the end caps to fasten the cable in tension within the device 10. In one embodiment, the cable ends are anchored by crimps 22 at each end, as depicted in FIGS. 3-4. Alternatively, the ends of the cable may be anchored to the end cap by clamping screws, such as the set screws described in published application 2005/0010220 to Casutt et al, for example. A passageway is defined through the end caps and spacer so that the cable may be wound through and around the components. In still other embodiments, one end of the cable may be provided with a fixed bead or stop, while the other end is crimped or clamped after passing through the end caps and spacer.

The anchored or crimped ends of the cable may be engaged to one end cap, such as end cap 14, while the cable forms a loop 24 through the opposite end cap, such as end cap 12. Tension in the cable holds the construct together. In certain preferred embodiments the device 10 is provided with a fixed end cap 12 and a slotted end cap 14 where active distraction of a vertebral segment is desired. However, it should be appreciated that the device 10 may include two fixed end caps 12 where no distraction is intended, or may include two slotted end caps 14 to achieve distraction from either or both ends of the device.

Details of the end caps 12 and 14 can be seen in FIGS. 5-11. Referring first to FIGS. 5-9, the fixed position end cap 12 includes a body 30 that defines a fastener bore 32 therethrough. The bore 32 has an engaging surface 34 with a diameter close to the diameter of the bone engaging fastener 20 extending therethrough. The bore thus holds the fastener in a fixed position within the end cap 12. The engaging surface 34 may have a variety of configurations to mate with corresponding features on the fastener, as described in more detail herein.

Figure 5:
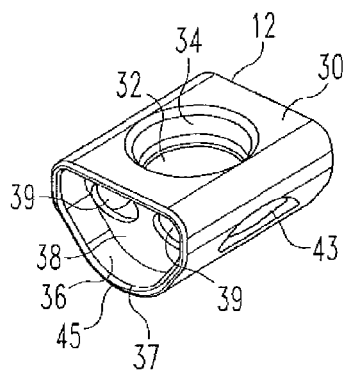
FIG. 5 is an end perspective view of an end cap component of the dynamic stabilization device depicted in FIG. 3.
Figure 6:
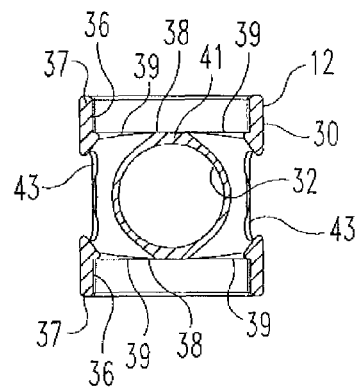
FIG. 6 is a top cross-sectional view of the end cap component illustrated in FIG. 5.
Figure 9:
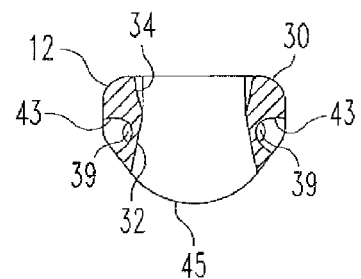
FIG. 9 is an end cross-sectional view of the end cap component shown in FIG. 8, as viewed along line 9-9.

The end cap 12 is preferably symmetric about a central transverse axis. Thus, each end defines an end recess 36 bounded at its perimeter by a rim 37, as best seen in FIGS. 5 and 6. The base of each recess is defined by an interior wall 38. Cable openings 39 are defined in each wall 38 for passage of the cable 18 wound through the end cap body. The cable passes through an opening and around a central hub 41 in the body 30. The fastener bore 32 is defined through the central hub, as seen in FIGS. 6 and 9. In one embodiment, the passageway for the cable around the hub 41 may include side notches 43. These notches may also be grasped by the arms of a gripping tool for manipulation and insertion of the stabilization device 10.

Figure 7:
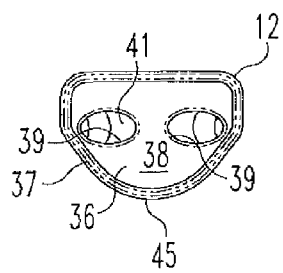
FIG. 7 is an end elevational view of the end cap component shown in FIG. 5.
Figure 8:
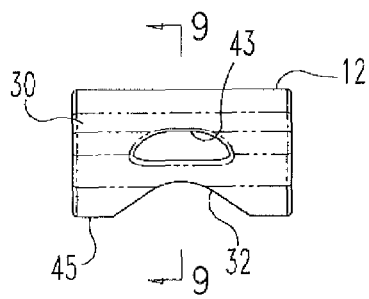
FIG. 8 is a side elevational view of the end cap component shown in FIG. 5.

As shown in FIGS. 7 and 9, the body 30 includes a contoured lower portion 45. This contoured portion is configured to fit snugly within the "gutter" formed by the transverse process and facet, as explained above. Thus, the contoured lower portion 45 not only helps the device maintain a low profile or prominence, it also enhances the stability of the implanted device.

Figure 10:
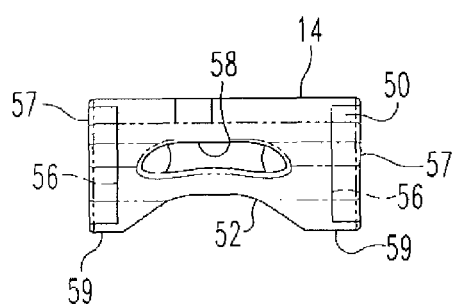
FIG. 10 is a side elevational view of another end cap component of the dynamic stabilization device depicted in FIG. 3.
Figure 11:
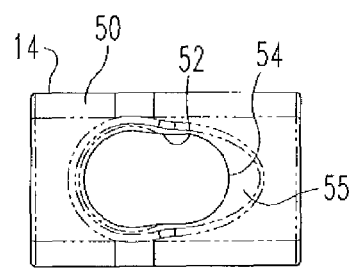
FIG. 11 is a top elevational view of the end cap component illustrated in FIG. 10.

As indicated above, the opposite end cap 14 in the illustrated embodiment is a slotted end cap, which means that it permits the fastener 20 to move relative to the device 10. In order to achieve this relative movement, the body 50 of the end cap 14 defines a fastener bore 52 that includes an elongated contoured slot 54, as shown in FIGS. 10 and 11. The slot 54 is aligned along the longitudinal axis of the end cap 14 and the device 10 so that the distance between the fasteners engaged at opposite ends of the stabilization device 10 may be changed. As explained in more detail below, this feature of the slotted end cap 14 allows the device to be used to distract the adjacent vertebrae while the device is implanted within the "gutter" and the fasteners are fully seated.

Like the end cap 12, the slotted end cap 14 defines end recesses 56 and perimeter rims 57 at the opposite ends. The body 50 further has the same construction for passage of the cable as in the body 30, including the cable openings, central hub, and side notches 58. Other than the elongated fastener slot 54, the end cap 14 may be identical in configuration to the end cap 12. For instance, the end cap 14 includes a contoured lower portion 59 similar to the lower portion 45 of the end cap 12 described above.

It is understood that both end caps 12 and 14 are sized and configured to fit within the "gutter" of a respective vertebra V1, V2. Thus, in a specific embodiment, the end caps have a width of about 0.475 in. and a depth of about 0.354 in. The width and depth dimensions, as well as the configuration of the lower portion 45 may be adjusted depending upon the instrumented level of the spine and the particular anatomy of the affected vertebrae. In a typical case, the lower portion 45 will have a generally trapezoidal shape, with the narrowest portion being somewhat rounded or curved, such as depicted in FIG. 5. The slotted end cap 14 is longer than the end cap 12 to accommodate the fastener engagement slot 54. In a specific embodiment, the slotted end cap 14 has a length of about 0.689 in., while the fixed end cap 12 has a length of about 0.551 in.

The dimensions of the fastener bores 32 and 52 are a function of the bone engaging fasteners 20 received therethrough. In one specific embodiment, the fixed diameter bore 32 has a diameter of about 0.264 in., with a countersink or flare of about 10-20°. The top portion of the bore may be further defined at a spherical radius of about 0.142 in., which is again dependent upon the dimensions of the head of the bone engaging fastener. As shown in FIG. 9, the flare at the bottom portion of the bore 32 accommodates a variable angular relationship between the fastener 20 and the end cap 12. The flared portion thus allows relative angulation between the end caps and the fastener in a transverse plane, as depicted in FIG. 2.

The elongated fastener bore 52 of the slotted end cap 14 maybe dimensioned to accept a similarly proportioned fastener 20. Thus, the ends of the slot may define surfaces at a radius of about 0.132 in. while the slot has a length of about 0.644 in. from end to end. The upper perimeter of the fastener engagement slot 54 is contoured, such as at portion 55 shown in FIG. 11 to engage the head of the fastener and direct the head of the fastener toward the free end of the end cap 14 in a camming action as the fastener is tightened into the bone.

In one embodiment, the end caps 12 and 14 are formed of a medical grade metal with sufficient strength to withstand typical spinal loads at the instrumented vertebral level. Suitable materials include stainless steel, titanium or alloys thereof, such as 6AL 4V titanium. Similarly, the cable 18 may be formed of the same material, such as wound or braided stainless steel strands or strands of a suitable high strength polymer. In one specific embodiment, the cable has an outer diameter of about 0.1 in. The selection of an appropriate material for the end caps and cable may be left to the person of ordinary skill in this art.

As shown in FIGS. 2-4, the device 10 includes a spacer 16 disposed between the two end caps 12 and 14. One embodiment of the spacer 16 is illustrated in FIG. 12. The spacer includes a body 70 with a pair of cable bores 72 extending therethrough along the length of the body. The opposite end faces 73 of the body 70 are configured to fit within the end recesses 36 and 56 of the end caps 12 and 14, respectively, as best shown in FIG. 4. In particular, the end faces 73 fit within the rims 37, 57 of the recesses. This fit may be a snug fit or a press-fit engagement. Alternatively, the end faces 73 of the spacer 16 and the end recesses 36, 56 may define a taper fit, such as at a Morse taper angle, to enhance the connection between the spacer and the end caps. Preferably, the lower portion 74 of the spacer body 70 is contoured to conform to the lower portion 45 of the end cap 12.

The spacer 16 may be preferably formed of a biocompatible elastomeric polymer that is sufficiently rigid along an axis parallel to the length of the spacer to serve in a preferred arrangement as a semi-rigid augment for fixation of a vertebral motion segment. Suitable materials for the spacer may include PEEK (polyetheretherketone), polyurethane, polyphenolsulfone, polysulfone, acetal (such as Delrin), polyethylene, as well as composites of these materials and carbon fibers. The selected material for the spacer must be capable of substantially resisting compression along the axis parallel to the length of the spacer between the end caps. This characteristic allows the spacer, and the entire stabilization device 10, to provide distraction at the instrumented segment. However, the elastomeric nature of the spacer preferably permits some compliance in all degrees of freedom. More particularly, the spacer is less rigid, or relatively more flexible, other than in compression, such as along axes other than the axis parallel to the length of the spacer. This property of the spacer thus provides dynamic stabilization to the spinal motion segment in extension, flexion and axial torsion. It can be noted that the amount of extension in the device during flexion may be a function of the elasticity of the cable.

The spacer 16 may be provided in a range of lengths corresponding to the spacing between the mounting locations at the adjacent vertebrae. As suggested above, a suitable mounting location for the fasteners 20 is the pedicle P of each vertebra V1, V2 (see FIG. 1). Thus, the length of the spacer 16 may be calibrated to a range of distances between pedicles, which will vary as a function of the instrumented vertebral level as well as the height and size of the patient. In one specific embodiment, it is contemplated that a set of predetermined lengths of spacers 16 may be provided with the end caps 12, 14. In another embodiment, a single length spacer may be provided that is cut to length prior to construction of the stabilization device 10. Thus, the spacer may have a length in the range about 0.5-1.5 inches or more, so that the fully constructed device 10 can have a length in the range of about 1.5-3.0 inches or greater.

The spacer 16 is connected to and held between the opposite end caps 12, 14, by a tension element, such as the cable 18, as shown in FIGS. 3-4. In one construction, the spacer and end cap components define a passageway for receiving the cable, beginning at one cable opening 53 (FIG. 3) in the slotted end cap 14. The spacer 16 is fitted within the end recess 56 of the slotted end cap so that the two cable bores 72 are aligned with the cable openings 53 in the end cap 14. Thus, the cable 18 follows the path from the opening 53 in the end cap, into one of the cable bores 72 in the spacer. The cable bores 72 in the spacer are also aligned with the cable openings 39 in the fixed position end cap 12 so that the cable exits the one cable bore and passes into one cable opening 39 of the end cap 12. The cable is then looped around the central hub 41 of the end cap 12 at loop 24 (FIG. 4) so that the cable returns through the other cable opening. The cable then passes back through the other cable bore 72 and the other cable opening 53 so that both ends of the cable 18 are situated at the exposed end of the end cap 14 (FIG. 3).

Preferably, one end of the cable 18 is fixed with a crimp 22 (as shown in FIG. 3), a brazed end or other suitable means for preventing passage of the cable through the cable opening 53 or otherwise anchoring the cable. With one end 18' of the cable essentially fixed against the end cap 14, the other end 18" of the cable is available for applying tension to the cable 18. Any appropriate tensioning tool may be used that permits tensioning the cable and fixation of the cable end by a crimp 22 or other suitable means for fixation. An exemplary tensioning tool is disclosed in U.S. Pat. No. 6,616,667 to Steiger et al. or in U.S. Pat. No. 5,395,374 to Miller et al. Once the cable 18 has been appropriately tensioned, a second crimp 22 or similar anchor is applied to the cable end 18" to thereby clamp the spacer 16 between the end caps 12 and 14 to complete the assembly of the device 10.

It should be understood that other mechanisms for anchoring the ends of the cable 18 to maintain its tension within the device 10 are contemplated. For instance, an end of the cable may be crimped directly to an end cap itself. Alternatively, the ends of the cable may be crimped together to form a single complete cable loop.

As shown in FIGS. 1-4, the device 10 is configured as an augment for a single vertebral level. As shown in FIGS. 15-16, the concepts of the present invention may be applied to two-level or multiple level augments. In particular, as shown in FIG. 15, an assembly 75 is configured to span between two vertebral levels for fixation to three successive vertebrae. The assembly 75 includes a stabilization device 10, assembled as described above with a spacer 16 flanked by the two end caps 12 and 14. In addition, the assembly 75 includes a modified stabilization device 76 that may include the same spacer 16 and slotted end cap 14 as described above. However, in lieu of the opposite end cap, the modified device 76 incorporates a boot 78 that is configured to fit over the end cap 16 of the device 10. This junction may include a taper, such as a Morse taper or other geometry capable of solid attachment.

In particular, the boot 78 includes a body 80 that defines a fastener opening 81 that preferably corresponds to the fastener bore 52 of the end cap 14 over which the boot is engaged. In other words, in the illustrated embodiment, the fastener opening 81 is elongated to match the elongated engagement slot 54 of the end cap 14. (It is understood that if the boot 78 fits over a fixed end cap 12, the fastener opening 81 may have a constant diameter).

The body 80 forms an end cap recess 84 that faces away from the spacer 70 and that terminates in an interior recess wall 85. The recess 84 has a length sufficient to substantially receive the end cap 14 so that the fastener bore 52 of the end cap may be aligned with the fastener opening 81 of the boot 78. In one specific embodiment, the end cap recess is sized for a snug fit between the end cap 14 and the boot. Alternatively, the recess 84 and end cap 14 may define a mating taper, such as a Morse taper. The mating taper configuration may prevent dislodgement of the boot from the end cap when the two components are pressed together.

The body 80 of the boot 78 further defines an end cap recess 82 opposite the elongated recess 84. The end cap recess 82 is configured to receive the spacer 16 in the manner described above. Thus, the end recess 82 may have the same configuration as the recesses 36 and 56 of the end caps 12 and 14, respectively.

The components of the boot 78 may be held together by a tensioned cable, such as the cable 18, in the same manner that the stabilization device 10 is held together as described above. Thus, the end cap 14 and spacer 16 define cable openings 53 and bores 72 for receiving the cable. Similarly, the boot 78 defines an interior cable wall 88 and loop cavity 89 in the interior wall 85 of the body 80. As shown in FIG. 16, the cable wall and cavity provide a path for the cable to loop through the boot 78, in the same manner that the cable loop 24 passes through the end cap 12 (as shown in FIG. 4). The modified stabilization device 76 may be assembled in the same manner as the device 10 by passing the cable 18 through the aligned cable openings and bores, forming a cable loop 24 within the boot 78 and crimping or fastening the ends of the cable at the end of the end cap 14.

It is contemplated that the two devices 10 and 76 are separately assembled, following selection of an appropriate length for the spacer 16 in each assembly. Once the two devices are assembled, the end cap 14 of the device 10 may be pressed into the boot 78 to form the complete two level assembly 75 shown in FIG. 15.

In the illustrated embodiments above, the stabilization device 10 and modified device 76 are assumed to be generally linear. However, in some instances the "gutter" formed by the processes of one vertebra is not in vertical alignment with the "gutter" of an adjacent vertebra. For instance in some cases the "gutter" of one vertebra may be rotated slightly relative to the "gutter" of an adjacent vertebra along the axis of the spine. In order to accommodate slight deviations or offsets between "gutter" positions of adjacent vertebrae, angled components are provided in certain embodiments.

In one embodiment, angled end caps may be provided, such as the end cap 60 shown in FIGS. 13 and 14. The end cap 60 includes a body 61 that defines a fastener bore 62 within a hub 66, in the same manner as the end caps 12 and 14 described above. Also, like the prior end caps, the end cap 60 includes opposite end recesses 63 with cable openings 65 defined therein for passage of a cable 18 through the end cap. However, unlike the prior end caps, the end recesses 63 are oriented at an angle B relative to the longitudinal axis of the end cap. This angle may range up to about 12° or more in certain embodiments, which has been found to be sufficient to account for typical deviations in "gutter" location between adjacent vertebrae.

It is understood that the angled end recesses 63 may be incorporated into end caps with fixed or elongated fastener bores. It is also contemplated that combinations of non-angled and angled end caps may be used in any particular construct as necessary to fit the anatomy of the instrumented vertebral motion segment. Thus, in some constructs, the stabilization device may include two oppositely angled end caps or one non-angled and one angled end cap.

The same concept may be applied to the multiple level instrumentation contemplated by the two level construct 75 shown in FIG. 15. In particular, the boot 78 may be modified as angled boot 90 shown in FIG. 18. This modified boot includes a recess 92 that is identical to the recess 84 of the boot 78 (FIG. 16). With this embodiment, the end recess 91 that mates with the spacer 16 is arranged at an angle C relative to the longitudinal axis of the boot. This angle C may range up to about 12° or more in certain embodiments.

Figure 19:
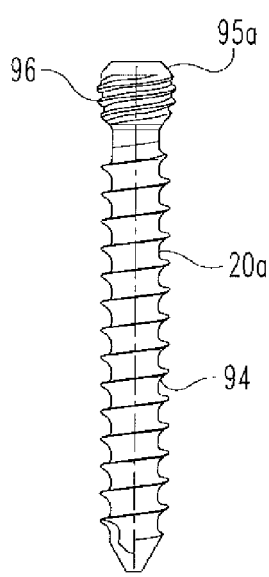
FIG. 19 is a side elevational view of a bone engaging fastener for use with the dynamic stabilization devices of the present invention.
Figure 20:
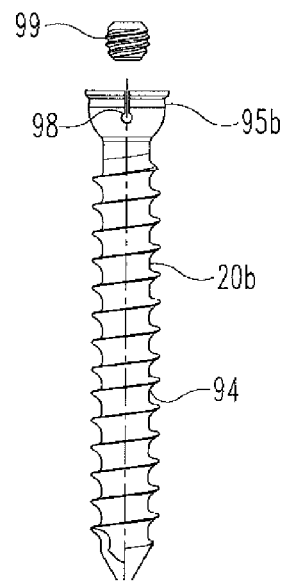
FIG. 20 is a side elevational view of an alternative bone engaging fastener for use with the dynamic stabilization devices of the present invention.
Figure 21:
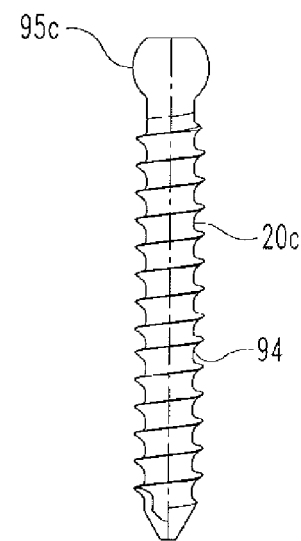
FIG. 21 is a side elevational view of yet another bone engaging fastener for use with the dynamic stabilization devices of the present invention.

As shown in FIGS. 1 and 2, the dynamic stabilization device 10 includes bone engaging fasteners 20 for fixing the device to the spine. In the preferred embodiment, the fasteners are cannulated bone screws adapted for threaded engagement within the vertebral body, particularly in the pedicle P. Various fastener configurations are contemplated which are capable of solid attachment of each end cap to the corresponding vertebra. As shown in FIGS. 19-21, each fastener 20a, 20b and 20c includes a threaded shank 94 with threads configured to be threaded into the vertebral bone. The threads may be self-tapping. The length of the threaded shank 94 of each fastener is determined by the vertebra into which the fastener is engaged.

Each fastener 20a, 20b, 20c also includes a corresponding head 95a, 95b and 95c that is configured to facilitate threading the fastener into bone. Thus, the head of each fastener may be provided with an internal or external hex for engagement by a driving tool. The head of each fastener is configured to achieve different forms of engagement to the corresponding end cap fastener bore 32, 52. For instance, in one form of engagement the head of the fastener is fixed within the bore. Thus, in one embodiment, the head 95a of the fastener 20a of FIG. 19 includes external threads 96. These threads may be configured to engage corresponding mating threads (not shown) defined in the fastener engagement surface 34 of the end cap 12. This particular embodiment is generally reserved for the fixed location end cap since the threads 96 require mating threads in the end cap fastener bore. It is contemplated that the threads 96 are smaller pitch threads than the bone engaging threads of the shank 94. An exemplary fastener and fastener bore of this type is described in U.S. Pat. No. 6,623,486 of Weaver et al., the disclosure of which is incorporated herein by reference Alternatively, the threads may be configured to cross-thread to achieve a solid attachment.

In an alternative embodiment shown in FIG. 20, the head 95b of the fastener 20b defines a collet 98. This collet 98 may configured to close as the head 95b is advanced deeper into the fastener bore 32, 52 of a corresponding end cap. Alternatively, the collet 98 is adapted to expand into an interference fit with the fastener bore by the action of a set screw 99 threaded into the collet.

In another form of engagement, such as the embodiment depicted in FIG. 21, the head 95c of the fastener 20c is a spherical head that seats within the engagement surface of the fastener bore. In one embodiment, the head is unconstrained relative to the bore, thereby permitting micro-movement or angulation of the bone screw relative to the end cap. In another embodiment, the spherical head 95c is held in place within the fastener bore by a snap ring or similar element. With this embodiment, the fastener bore 32, 52 is modified to include a snap ring groove for receiving the snap ring. In a specific embodiment, the snap ring is positioned within the ring groove as the fastener 20c is passed through the end cap and threaded into the bone. As the head 95c passes the snap ring, it expands the ring outward until the head is below the ring. At this point, the ring snaps inward to its original configuration and diameter, thereby trapping the head 95c of the fastener within the end cap. It is understood that the bone engaging fasteners shown in FIGS. 19-21 are intended to be exemplary and that other suitable fasteners may be used with the stabilization devices of the present invention.

Figure 22:
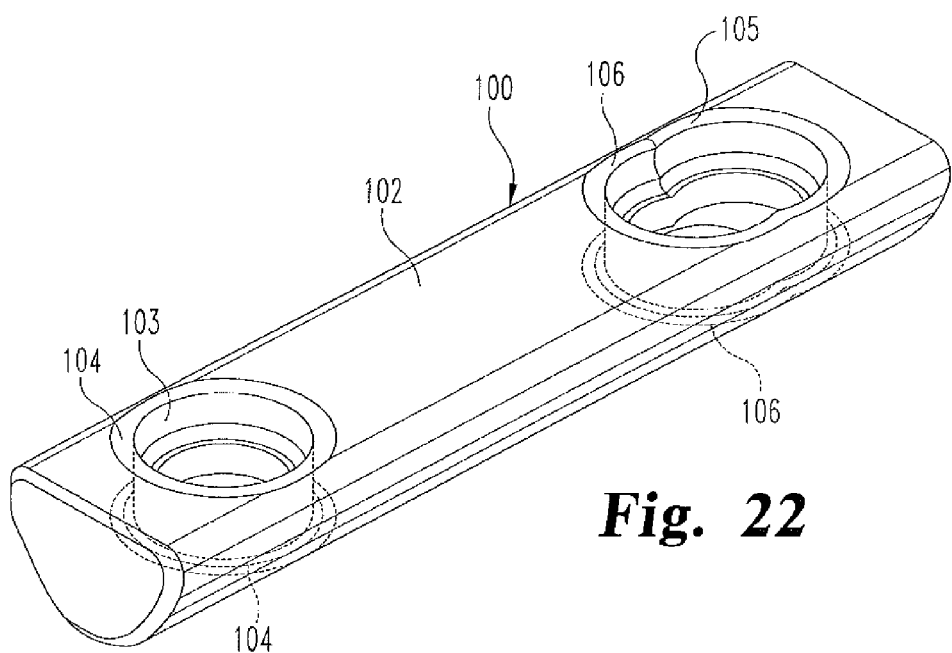
FIG. 22 is a top perspective view of a dynamic stabilization device according to another embodiment of the present invention.

In a further embodiment illustrated in FIG. 22, a stabilization device 100 includes a molded polymer body 102 and metal fastener bushings 103 and 105. One of the bushings 103 provides a fixed diameter opening similar to the end cap 12 for engaging a fastener, such as the fasteners 20a-20c described above. The other bushing 105 may be provided with a slotted contoured opening, similar to the slotted end cap 14 for engaging a fastener. Each bushing 103, 105 may be preferably provided with an engagement rim 104, 106, respectively, on the upper and lower edges of the bushing. The engagement rims anchor the bushings 103, 105 within the molded polymer body.

In this embodiment, the polymer body 102 is over-molded around the bushings to form a unitary structure. The molding process may occur in a variable length mold having the exterior shape of the end caps 12, 14 described above. The mold supports the bushings 103, 105 at variable relative distances so that the resulting stabilization device 100 may be tailored to the particular anatomy of the instrumented vertebral level. The device 100 may be combined with the modified device 76 to form a two level or other multi-level construct in the manner described above. The polymer body 100 may be made of any of the materials discussed above for the spacer 16.

Figure 23:
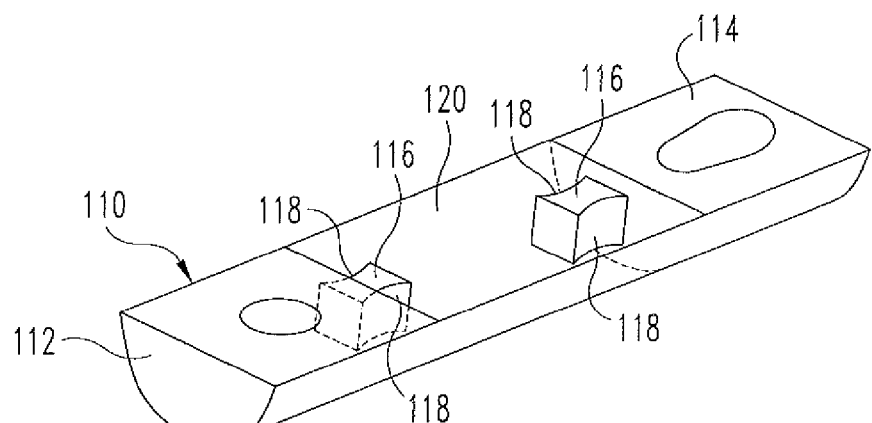
FIG. 23 is a top perspective view of a dynamic stabilization device according to yet another embodiment of the present invention.

An alternative molded construct depicted in FIG. 23 contemplates a device 110 having opposite end caps 112, 114, with the inboard end of each end cap defining a projection 116. The projection 116 includes contoured surfaces 118, such as in the shape of a mushroom. The device 110 further includes a spacer 120 that is over-molded around the projections 116. The contoured shape of the projections help retain the connection between the spacer and the end caps. The end caps 112, 114 may be configured like the end caps 12, 14 described above with appropriate modifications to add the contoured projections 116.

Figure 24:
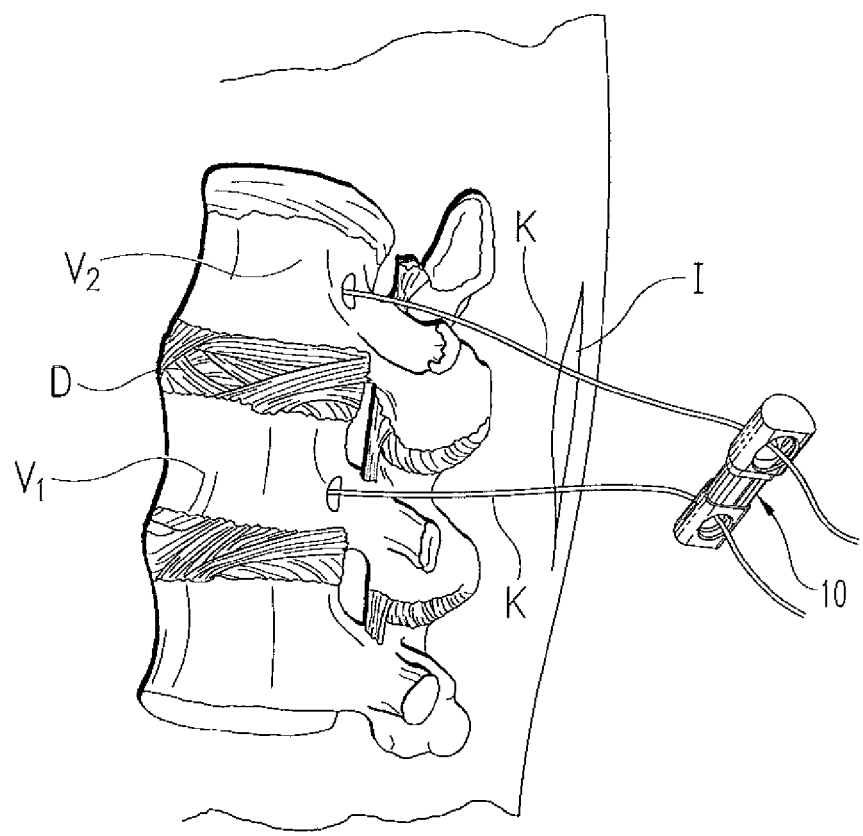
FIG. 24 is a lateral pictorial representation of one step in a method for implanting a dynamic stabilization device in accordance with the present invention.

The present invention contemplates a minimally invasive surgical procedure for implanting any of the above-disclosed dynamic stabilization devices 10, 75, 100 or 110 within the patient. While the devices of this invention are preferably for use in the lumbar spine, variations may be used in the thoracic or cervical spine. For the procedure, the patient is initially positioned on a surgical table and fluoroscopy is used to verify the orientation of the vertebral level to be instrumented. The pedicles P of the vertebrae V1, V2 are then located under fluoroscopy and a small incision I is made through the spin. The tissues are bluntly dissected to expose the "gutter" of the pedicles to be instrumented. A K-wire K is next introduced into each pedicle, as shown in FIG. 24.

It is contemplated that the incision I is as small as practical between the K-wires to minimize the surgical intrusion. However, the incision is preferably large enough to permit introduction of a measuring instrument adapted to measure the distance between the K-wires at the pedicles. Although the distance between the wires K may be roughly determined by indirect imaging (such as fluoroscopy), it may be desirable that the distance be directly measured. Thus, this distance may be obtained using a suitable measuring instrument, such as for example the measuring instruments disclosed in published application No. 2004/0267279 in the name of Casutt et al.

It is further contemplated that the incision will be less than the distance between the locations on the vertebral bodies where is it anticipated that the bone screws will be introduced. In a typical procedure, those locations will be the pedicles of the adjacent vertebrae. Thus, the incision I is preferably shorter than the anticipated inter-pedicle distance, which will of course vary depending upon the patient and the instrumented level. In a specific embodiment, the incision I can have a length of about 1-2 inches. If necessary, the surgeon may manipulate the incision somewhat during the procedure to accommodate the measuring instrument and/or the stabilization device, and to provide access to the implantation site.

Once the distance between pedicles is known, the dynamic stabilization device may be prepared. In the case where the stabilization device is provided in predetermined lengths, such as the device 100 shown in FIG. 22, the pedicle distance measurement may be used to select a device corresponding to the inter-pedicle distance.

Figure 25:
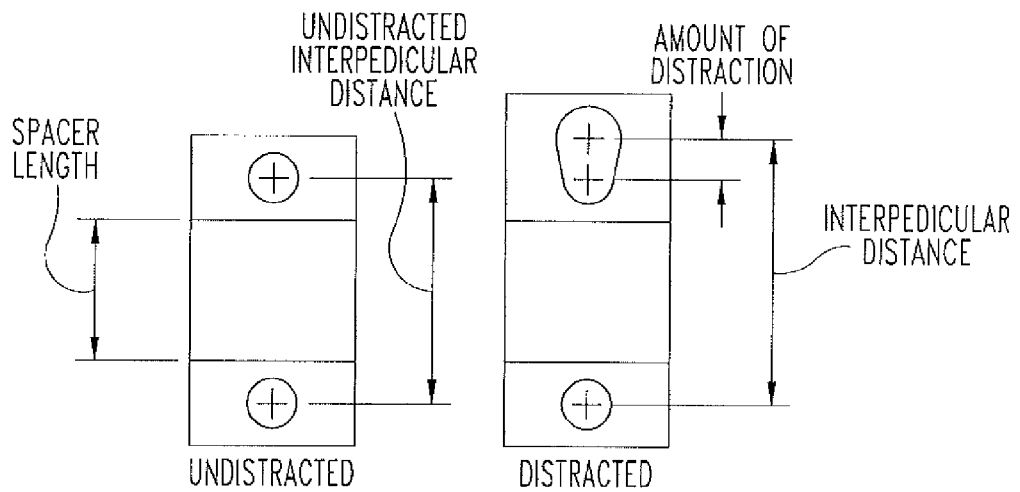
FIG. 25 is a pictorial representation of one method for selecting the length of spacer to be used in the dynamic stabilization devices of the present invention.

In the embodiments constructed according to the device 10 shown in FIG. 2, the inter-pedicle distance information is thus used to select or prepare an appropriately sized spacer 16. It is contemplated that the stabilization device 10 may be provided as part of a kit that includes at least one fixed and one slotted end cap 12 and 14, respectively, along with a selection of spacers 16 of different lengths. Referring to FIG. 25, the spacer selection is based on the distance in the end cap-spacer-end cap assembly from the center of the anchoring hole in the fixed end cap to the center of the inboard radius of the slot in the slotted end cap. For the proper spacer, this distance will be equal to the inter-pedicle distance measured as explained above. Due to the tapered geometry of the slot, the screw and the vertebral body into which the screw is driven will be forced to the outboard end of the slot (i.e., away from the fixed end cap), resulting in distraction of the vertebral level as the screw is driven into the pedicle.

It is also contemplated that in certain applications, such as where no distraction is desired, the end cap-spacer-end cap assembly may include two fixed position end caps. In this situation, a spacer is preferably selected which results in the center-to-center distance between the anchoring holes of the end caps being equal to the measured inter-pedicular distance.

Once the spacer has been selected, the stabilization device 10 may be assembled on a staging table. Thus, a tension cable may be threaded through one end cap, such as end cap 14, through one cable bore 72 in the spacer, through the other end cap, such as end cap 12, to form a cable loop, back through the other cable bore in the spacer and exiting from the original end cap. The trailing end of the cable 18 may be provided with a crimp or other feature that bears against the end cap when the free end of the cable is pulled taut. The free end of the cable 18 may be tensioned and a crimp or other fixation feature engaged to the cable to maintain the cable in tension and complete the assembly of the device 10.

The assembled device 10 is then passed over the guide wires K, as shown in FIG. 24. In the preferred embodiment, the K-wire passes through the fastener bore 32, 52 in each end cap 12, 14 of the assembled device. The device 10 and guide wires K may be manipulated so that the device is guided through the incision I at an angle—i.e., with one end of the device entering the incision I first. With this approach, the length of the incision I may be kept to a minimum since it does not need to have a length equal to or greater than the length of the stabilization device 10.

Figure 26:
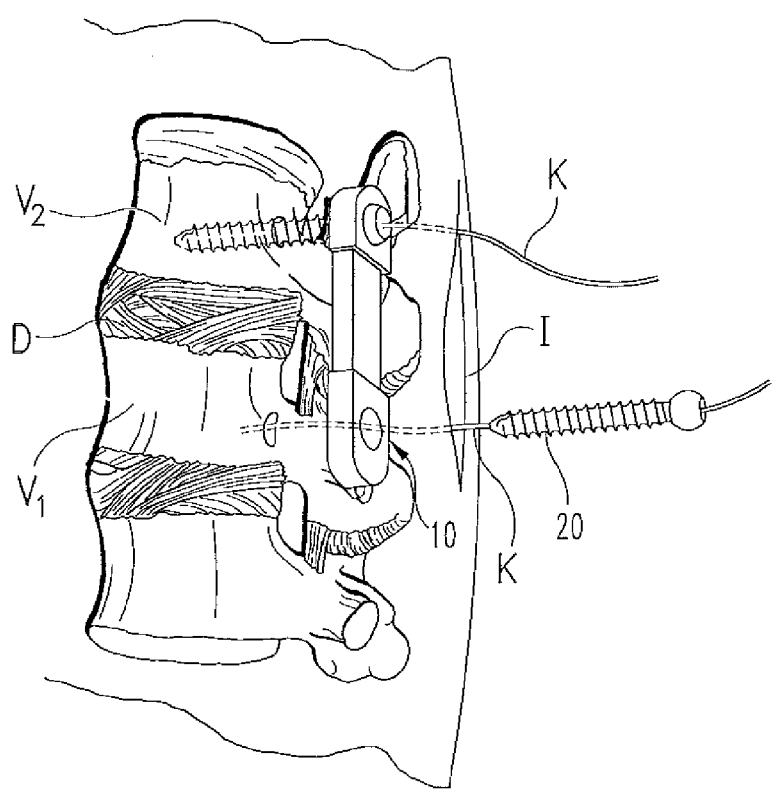
FIG. 26 is a lateral pictorial representation of another step of the method for implanting the dynamic stabilization device of the present invention.

It can be appreciated that the K-wires may be flexed slightly to accomplish this manner of introduction of the device 10. As the device 10 is moved nearer to the vertebrae V1, V2, the orientation of the device will naturally move toward its proper alignment relative to the spine, as depicted in FIG. 26. Once the device 10 has been positioned with the "gutter" of the vertebrae V1, V2, the cannulated bone engaging fasteners 20 may be introduced over each K-wire.

In one embodiment, a fastener is passed through the fixed position end cap, such as end cap 12, and threaded into the vertebra V1. With one end of the stabilization device anchored to the first vertebra, the second fastener may be passed along the guide wire K through another end cap, which may also be end cap 12. In this embodiment, the second fastener is tightened to its prescribed torque and the instrumentation is complete.

In the preferred embodiment, the device 10 is used to distract the two vertebrae V1, V2. In this instance, the device 10 includes an end cap 12 at one end and a slotted end cap 14 at the other end. The first fastener is threaded into the pedicle through the fixed end cap 12, as described above. As the second fastener is threaded into the pedicle over the K-wire, the contoured slot 54 will displace the fastener toward the free end of the end cap 14. While there will be some compression of the spacer 16, there will also be sufficient resistance that will cause distraction of the vertebral segment as the fastener is driven to the distal end of the slot upon tightening. In a particular use, the geometry of the slot 54 is such that the fastener may be displaced approximately 2 mm. Of course, other slot geometries may be utilized to provide other suitable fastener displacements for a desired distraction.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For instance, in the illustrated embodiments a single cable 18 is used to couple each of the components 12, 14, and 16 together to form the stabilization device 10. Alternatively, a plurality of cables may be utilized in several different ways to couple the components. For instance, a second cable may be wound through the end caps and spacer from the opposite direction, provided that the cable openings 39, 53 and cable bores 72 are appropriately sized. As a further alternative, a second set of cable openings and bores may be provided to accept the second cable. In yet another alternative, a plurality of cables may extend from end to end of the device in the absence of a cable loop 24, with each end crimped or fastened to a corresponding one of the opposite end caps.

It should also be understood that while the preferred embodiment of the device 10 has been described herein for use as a semi-rigid augment to spinal fixation, the device may also be used as a rigid augment. In this case, the spacer 16 may be formed of a substantially rigid material, such as a metal or a stiff polymer, and may be used with or without distraction.

What is claimed is

1. A stabilization device for implantation in the spine of a patient, comprising:
    a pair of rigid end pieces, each defining a bore for receiving a bone engaging fastener therethrough, the end pieces each including a lower portion that is contoured with a generally trapezoidal shape to rest snugly within a gutter formed by a transverse process and a facet of a corresponding vertebra of the patient; and
    an elongated spacer engaging each of the end pieces to maintain the end pieces at a predetermined spacing relative to each other, the spacing adapted to orient the bore of each of the end pieces with respect to a corresponding vertebra of the patient, the spacer being substantially rigid in compression along an axis parallel to the length of the spacer between the end pieces and relatively more flexible other than in compression.

2. The stabilization device of claim 1, wherein the spacer is formed of a material selected from PEEK (polyetheretherketone), polyurethane, polyphenolsulfone, polysulfone, acetal (including Dehin), polyethylene, and composites thereof.

3. The stabilization device of claim 1, wherein:
    each of the pair of end pieces is a bushing; and
    the elongated spacer is an elastomeric body over-molded about the end pieces.

4. The stabilization device of claim 1, wherein:
    the elongated spacer is an elastomeric body; and
    each of the pair of end pieces is an elongated end cap having an end recess configured to receive an end of the elastomeric body therein.

5. The stabilization device of claim 4, wherein the end recess of at least one of the pair of end caps is oriented at an angle relative to a longitudinal axis of the end cap.

6. The stabilization device of claim 4, further comprising a tensioning element coupling the spacer to the pair of end caps.

7. The stabilization device of claim 6, wherein:
    the tensioning element includes a cable;
    the spacer and pair of end caps define a passageway for receiving the cable in a loop therearound; and
    the ends of the cable include an element for anchoring the cable to at least one of the end caps.

8. The stabilization device of claim 4, wherein one of the pair of end caps includes an end cap recess defined at a face of the end cap facing away from the spacer, the end cap recess sized to receive an end cap of another stabilization device therein to form a multi-level construct.

9. The stabilization device of claim 8, wherein the end recess of the one end cap is oriented at an angle relative to the end cap recess.

10. The stabilization device of claim 4, wherein the elongated spacer is selectable from a plurality of elastomeric bodies having different lengths.

11. The stabilization device of claim 1, wherein the spacer includes a lower portion that is contoured substantially similar to the lower portion of the end pieces.

12. The stabilization device of claim 11, wherein said spacer is substantially linear and extends between said end pieces in substantial alignment with said bores.

13. The stabilization device of claim 1, further comprising a pair of bone engaging fasteners, each configured to extend through the bore of a corresponding one of the pair of rigid end pieces.

14. The stabilization device of claim 13, wherein each of the bone engaging fasteners is a bone screw having a threaded shank configured for threaded engagement in vertebral bone and a head sized to prevent passage through the bore.

15. The stabilization device of claim 14, wherein:
    the bore includes a fastener engagement surface; and
    the head of the bone screw and the engagement surface are mutually configured to permit orientation of the bone screw at a range of angles relative to the end piece.

16. The stabilization device of claim 14, wherein:
    the bore includes a fastener engagement surface; and
    the head of the bone screw and the engagement surface are mutually configured to permit fixation of the head of the bone screw relative to the end piece.

17. The stabilization device of claim 1, wherein:
    each of the end pieces is an elongated end cap having a projection extending from an end face thereof; and
    the elongated spacer is an elastomeric body over-molded about the projection of each of the end caps.

18. The stabilization device of claim 1, wherein the narrowest portion of the lower portion of said generally trapezoidal shape of said end pieces are generally rounded or curved.

19. A stabilization device for implantation in the spine of a patient, comprising:
   a pair of rigid end pieces, each defining a bore for receiving a bone engaging fastener therethrough, the bore of at least one of the pair of end pieces being elongated parallel to the axis; and
   an elongated spacer engaging each of the end pieces to maintain the end pieces at a predetermined spacing relative to each other, the spacing adapted to orient the bore of each of the end pieces with respect to a corresponding vertebra of the patient, the spacer being substantially rigid in compression along an axis parallel to the length of the spacer between the end pieces and relatively more flexible other than in compression,
   wherein the elongated bore defines a slot configured to receive the head of a bone engaging fastener extending through the elongated bore, the slot being contoured with a camming surface to move the head of the fastener away from the spacer as the fastener extends farther into the bore.

20. The stabilization divice of claim 19, wherein the bore of the at least one of the pair of end pieces that is enlongated parallel to the axis comprises a tapered geometry.

21. A stabilization device for implantation in the spine of a patient, comprising:
   a pair of rigid end pieces, each defining a bore for receiving a bone engaging fastener therethrough, the bore of at least one of the pair of end pieces comprising a tapered geometry, each of the pair of end pieces being an elongated end cap having an end recess;
   an elongated spacer engaging each of the end pieces to maintain the end pieces at a predetermined spacing relative to each other, the spacing adapted to orient the bore of each of the end pieces with respect to a corresponding vertebra of the patient, the spacer being substantially rigid in compression along an axis parallel to the length of the spacer between the end pieces and relatively more flexible other than in compression, the elongated spacer being an elastomeric body having ends received respectively in a recess of an end cap; and
   a tensioning element coupling the spacer to the pair of end caps, the tensioning element including a cable, the spacer and said pair of end caps defining a passageway for receiving the cable in a loop therearound, the ends of the cable including an element for anchoring the cable to at least one of the end caps, wherein the element includes a crimp formed at each end of the cable, each crimp engaging one of the pair of end caps to maintain the cable in tension within the passageway.

* * * * *

UNITED STATES PATENT AND TRADEMARK OFFICE
CERTIFICATE OF CORRECTION

PATENT NO. : 7,993,375 B2
APPLICATION NO. : 11/950754
DATED : August 9, 2011
INVENTOR(S) : Hyun Bae et al.

It is certified that error appears in the above-identified patent and that said Letters Patent is hereby corrected as shown below:

IN THE SPECIFICATIONS:

Column 4, line 41, replace "orientation sin order to" with --orientations in order to--.

Column 13, line 49, replace "incision I is made through the spin" with --incision I is made through the spine--.

Signed and Sealed this
Twenty-fifth Day of October, 2011

David J. Kappos
*Director of the United States Patent and Trademark Office*